(12) United States Patent
Richmond et al.

(10) Patent No.: US 11,830,183 B2
(45) Date of Patent: Nov. 28, 2023

(54) TREATMENT PLANNING BASED ON MULTIMODAL CASE SIMILARITY

(71) Applicant: Merative US L.P., Ann Arbor, MI (US)

(72) Inventors: David Richmond, Newton, MA (US); Amin Katouzian, Lexington, MA (US); Maria Victoria Sainz de Cea, Somerville, MA (US); Sun Young Park, San Diego, CA (US)

(*) Notice: Subject to any disclaimer, the term of this patent is extended or adjusted under 35 U.S.C. 154(b) by 351 days.

(21) Appl. No.: 17/011,556

(22) Filed: Sep. 3, 2020

(65) Prior Publication Data

US 2022/0067926 A1    Mar. 3, 2022

(51) Int. Cl.
| | | |
|---|---|---|
| *G06F 17/00* | (2019.01) | |
| *G06F 7/00* | (2006.01) | |
| *G06T 7/00* | (2017.01) | |
| *G06N 20/00* | (2019.01) | |
| *G06F 16/583* | (2019.01) | |
| *G06V 10/40* | (2022.01) | |

(52) U.S. Cl.
CPC .......... *G06T 7/0012* (2013.01); *G06F 16/583* (2019.01); *G06N 20/00* (2019.01); *G06V 10/40* (2022.01); *G06T 2207/20081* (2013.01)

(58) Field of Classification Search
CPC ......... G06T 7/0012; G06T 2207/20081; G06F 16/583; G06N 20/00; G06V 10/40
USPC ........................................................ 707/698
See application file for complete search history.

(56) References Cited

U.S. PATENT DOCUMENTS

| | | | |
|---|---|---|---|
| 7,298,881 B2 | 11/2007 | Giger et al. | |
| 7,797,282 B1 * | 9/2010 | Kirshenbaum | G06F 16/35 |
| | | | 707/681 |
| 8,688,618 B2 | 4/2014 | McNutt et al. | |
| 9,047,290 B1 * | 6/2015 | Kirshenbaum | G06N 5/00 |
| 9,721,338 B2 | 8/2017 | Madabhushi et al. | |
| 2009/0110192 A1 | 4/2009 | Elrod et al. | |
| 2010/0063947 A1 | 3/2010 | Burnside et al. | |

(Continued)

FOREIGN PATENT DOCUMENTS

| | | |
|---|---|---|
| WO | 2009083833 A1 | 7/2009 |
| WO | 2016032503 A1 | 3/2016 |

OTHER PUBLICATIONS

"Evaluation of Automatic Class III Designation for QuantX," Decision Summary, De Novo Summary DEN170022, 2017, pp. 1-24.

(Continued)

*Primary Examiner* — Pavan Mamillapalli
(74) *Attorney, Agent, or Firm* — Stephen J. Walder, Jr.

(57) ABSTRACT

A system, method, and computer program product for treatment planning are disclosed. The system includes at least one processing component, at least one memory component, a training module, a retrieval module, and a plan generator. The training module generates hash codes by hashing features from data sources with data source-specific hash functions, and generates superclass hash codes by hashing the generated hash codes with at least one superclass hash function. The retrieval module extracts features from case data, and locates features from the data sources that are similar to the extracted features. The plan generator calculates outcome probabilities for the case data based on known outcomes associated with the located features.

20 Claims, 5 Drawing Sheets

(56) References Cited

U.S. PATENT DOCUMENTS

| | | | |
|---|---|---|---|
| 2013/0268547 A1* | 10/2013 | Boroczky | G16H 50/70 707/758 |
| 2014/0064580 A1 | 3/2014 | Madabhushi et al. | |
| 2017/0193660 A1 | 7/2017 | Schmidt et al. | |
| 2019/0220978 A1 | 7/2019 | Moehrle et al. | |
| 2019/0236782 A1* | 8/2019 | Amit | G06T 7/0016 |

OTHER PUBLICATIONS

A. Fornells et al., "Patterns Out of Cases Using Kohonen Maps in Breast Cancer Diagnosis," International Journal of Neural Systems, vol. 18, No. 1, pp. 33-43, 2008.

A. Holzinger, "Machine Learning and Knowledge Extraction in Digital Pathology Needs an Integrative Approach." In: Holzinger A., Goebel R., Ferri M., Palade V. (eds.) Towards Integrative Machine Learning and Knowledge Extraction. Lecture Notes in Computer Science, vol. 10344. Springer, Cham, pp. 13-50, 2017.

F. Ma et al., "Mammogram Mass Classification with Temporal Features and Multiple Kernel Learning," 2015 International Conf. on Digital Image Computing: Techniques and Applications (DICTA), Adelaide, SA, 2015, pp. 1-7.

L. Hadjiiski et al., "Analysis of temporal changes of mammographic features: Computer-aided classification of malignant and benign breast masses." Med Phys., Nov; 28(11): 2309-17, 2001.

Mell et al., "The NIST Definition of Cloud Computing," Recommendations of the National Institute of Standards and Technology, U.S. Department of Commerce, Special Publication 800-145, Sep. 2011, 7 pgs.

S. Timp et al., "Temporal Change Analysis for Characterization of Mass Lesions in Mammography," in IEEE Transactions on Medical Imaging, vol. 26, No. 7, pp. 945-953, Jul. 2007.

T. Kooi and N. Karssemeijer, "Classifying Symmetrical Differences and Temporal Change in Mammography Using Deep Neural Networks," (Submitted on Mar. 22, 2017 (v1), last revised Aug. 1, 2017 (this version, v2)), https://arxiv.org/abs/1703.07715.

J. Xu et al., "Federated Patient Hashing" The Thirty-Fourth AAAI Conference on Artificial Intelligence, 2020, pp. 6486-6493.

* cited by examiner

TREATMENT PLANNING BASED ON MULTIMODAL CASE SIMILARITY

BACKGROUND

The present disclosure relates to computer-assisted clinical decision making and, more specifically, to personalized treatment planning based on multimodal similarity matching.

Clinical decision making, such as treatment planning, can be aided by health information technology systems that use techniques from machine learning, data science, etc. For example, computer-aided diagnosis (CADx) systems can provide support in the interpretation of medical images (e.g., images from X-ray, ultrasound, magnetic resonance imaging (MRI), etc.). Clinical decision support (CDS) systems can output information in response to user-input information about a patient's case. For example, CDS systems can generate case-specific responses using knowledge-based or machine learning techniques (e.g., artificial neural networks, support-vector machines, genetic algorithms, etc.). The responses can be based on the user-input information and information from healthcare databases, statistical methods, etc. The responses can offer suggestions for treatments, predicted outcomes, etc.

SUMMARY

Various embodiments are directed to a system for treatment planning that includes at least one processing component, at least one memory component, a training module, a retrieval module, and a plan generator. The training module generates hash codes by hashing features from data sources with data source-specific hash functions, and generates superclass hash codes by hashing the generated hash codes with at least one superclass hash function. In some embodiments, the training module generates higher level superclass hash codes by hashing a group of the superclass hash codes with at least one higher level superclass hash function. The training module can also generate a machine learning module trained on the superclass hash codes, as well as a machine learning module trained on the higher level superclass hash codes. The retrieval module extracts features from case data, and locates features from the data sources that are similar to the extracted features. The retrieval model can also generate query hash codes by hashing features from the extracted features with superclass hash functions and/or higher level superclass hash function. The features from the data sources and/or the case data can include longitudinal sequences, such as sequences based on series of medical images. The plan generator calculates outcome probabilities for the case data based on known outcomes associated with the located features.

Further embodiments are directed to a method that includes generating hash codes by hashing features from data sources with data source-specific hash functions, and generating superclass hash codes by hashing the generated hash codes with at least one hash function. The method also includes extracting features from case data, locating features from the data sources that are similar to the extracted features, and calculating outcome probabilities for the case data based on known outcomes associated with the located features. In some embodiments, the method also includes generating higher level superclass hash codes by hashing a group of the superclass hash codes with at least one higher level superclass hash function. Additionally, the method can include generating a machine learning module trained on the superclass hash codes. The method can include generating query hash codes by hashing features from the extracted features with superclass hash functions and/or higher level superclass hash function. The features from the data sources and/or the case data can include longitudinal sequences, such as sequences based on series of medical images.

Additional embodiments are directed to a computer program product for treatment planning. The computer program product includes a computer readable storage medium having program instructions embodied therewith, the program instructions executable by a processor to cause a device to perform a method. The method includes generating hash codes by hashing features from data sources with data source-specific hash functions, and generating superclass hash codes by hashing the generated hash codes with at least one hash function. The method also includes extracting features (e.g., longitudinal sequences) from case data, locating features from the data sources that are similar to the extracted features, and calculating outcome probabilities for the case data based on known outcomes associated with the located features. In some embodiments, the method also includes generating higher level superclass hash codes by hashing a group of the superclass hash codes with at least one higher level superclass hash function.

DETAILED DESCRIPTION

Health information technology systems can include systems that use machine learning and data science techniques to help medical professionals make decisions regarding individual cases based on data gathered from similar cases. For example, medical images, lab results, and treatment outcomes from a large number of cases can be stored. A medical professional can enter information for a particular individual's case, and receive a response generated by a treatment planning system using knowledge-based and/or machine learning techniques (e.g., artificial neural networks, support-vector machines, genetic algorithms, etc.). For example, a radiologist can input an X-ray image into a computer-aided diagnosis (CADx) system that accesses a database of X-ray images with previously identified features. The CADx system can then use machine learning techniques to help the radiologist interpret regions of interest in the input X-ray image. For example, the CADx system can use a machine learning model trained on data from the database of identified X-ray images. The model can use statistical methods to determine which interpretations (e.g., benign, malignant, unknown, etc.) are most likely to be accurate based on similarity matching between the input image and images in the database.

However, machine learning models for health information technology systems such as these are limited by the availability of accurate and complete training data. For example, ground truth annotation of the training data must be carried out by qualified medical specialists. Further, the anonymity of patients must be maintained when extracting information from any data source, and privacy policies can forbid sharing patients' information across institutions. Additionally, due to the complexity inherent in diagnosing and treating medical conditions, even small amounts of incomplete or inaccurate information in the training data can significantly reduce the efficacy of the information generated. Thus, there is a need for techniques that can improve similarity matching and prevent users from receiving suggestions based on inadequate information.

Disclosed herein are techniques for generating personalized treatment plans based on multimodal information that can come from more than one data source. Obtaining the data does not require transfer of patients' information across institutions. Instead, data source-specific hash functions are generated for each data source, and used to hash features of the data. The resulting hash codes can then be hashed by superclass hash functions to generate multiple levels for different modalities. Hash codes generated by the data source-specific and superclass hash functions are used to train a retrieval model for matching similar cases. Therefore, the treatment planning system can locate relevant data for evaluating an input case based on hash code similarity, without accessing the raw patient-level data. Additionally, the treatment planning retrieval model can search large amounts of data without needing to extract the data or generate and store hash functions for the data. This allows the treatment planning system retrieval model to conduct faster searches, and it requires less memory consumption. Longitudinal sequences based on series of data for individuals can be determined for various modalities. Different modalities can include biometric data, clinical notes, medical images, etc.

Figure 1:
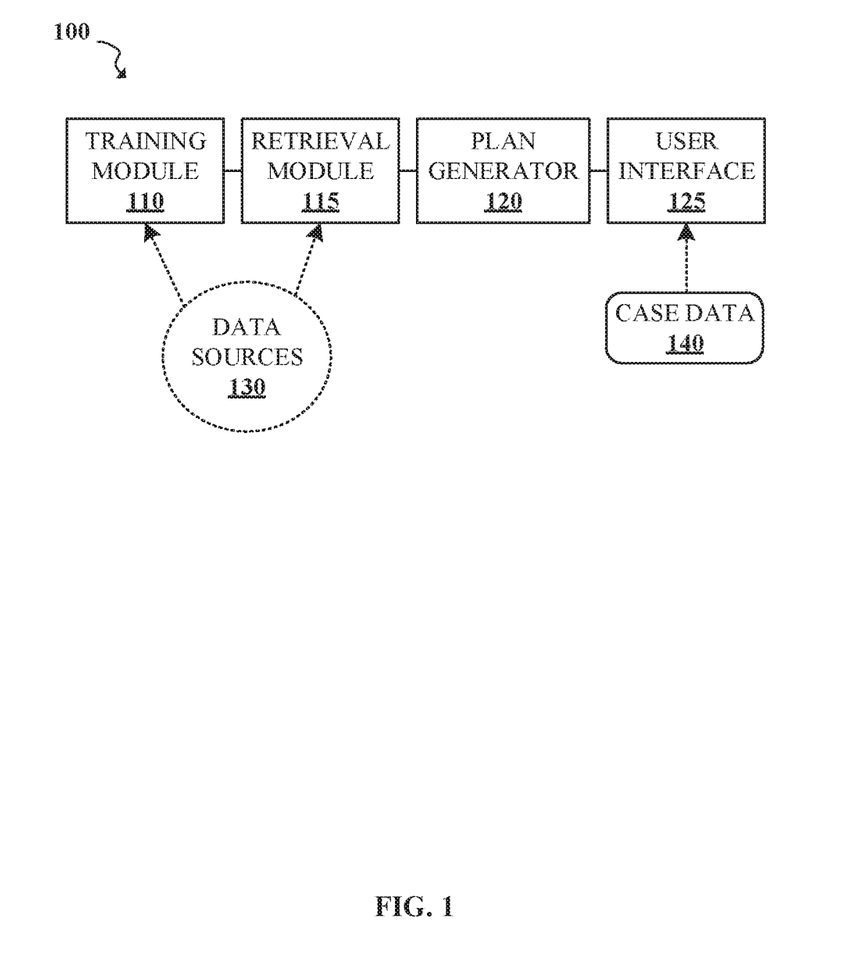
FIG. 1 is a block diagram illustrating a treatment planning environment, according to some embodiments of the present disclosure.

FIG. 1 is a block diagram illustrating a treatment planning environment 100, according to some embodiments of the present disclosure. The treatment planning environment 100 includes a training module 110, a retrieval module 115, a plan generator 120, and a user interface 125. The treatment planning environment 100 also includes data sources 130 and case data 140. The data sources 130 provide training data for the training module 110, and the case data 140 is user-input data for a particular patient's case.

There can be two or more data sources 130. Each of the data sources 130 can provide at least one type of data related to treatment planning. For example, data sources 130 can include X-ray and/or other medical image (e.g., MRI) databases, clinical research publications, fitness-tracking wearable device data, lab test results, prescription records, patient background information (e.g., age, medical history, etc.), etc. Additionally, each data source 130 can be associated with at least one institution and/or category. For example, one data source 130 can be a set of X-ray images from a first clinic, and another data source 130 can be a set of X-ray images from a second clinic. Further, information related to particular individuals can be stored in more than one of the data sources 130. For example, computed tomography (CT) scans from one patient can be stored in at least one CT scan database (data source). If the patient has had CT scans taken at more than one clinic, each clinic may store its own CT scan database. Other data sources 130 can store information related to this patient as well. For example, a set of clinical notes can include notes associated with this patient (e.g., descriptions of treatments and their outcomes).

The training module 110 can extract features from the data sources 130. However, in some embodiments the features are already hashed at the data source, and the training module 110 extracts the hash codes generated by the pre-existing hash data source-specific hash function. The features can include structured and/or unstructured data. For example, features extracted from an MRI scan database can include image features (e.g., signal intensities in different regions of the images), image interpretation features (e.g., types of tissues, regions identified as possible abnormalities, diagnoses of identified abnormalities, etc.), identifying features (e.g., patient or case number, date and time of scan, etc.), and/or MRI scanning information (e.g., sequencing type, signal processing information, MRI hardware information, etc.). Features similar to those extracted from the MRI database can be extracted from the CT scan database (e.g., CT scan images features, image interpretation features, case identifying features, CT scanning information, etc.).

The features can include longitudinal features. For example, a data source 130 can include multiple X-ray images of the same patient, each depicting the same region of interest (e.g., a lesion), which were collected at intervals over a period of time. A longitudinal sequence can be generated from these images, and hashed with the appropriate data source-specific hash function. Other longitudinal sequences that can be generated can include information about the development of symptoms or responses to treatments over time. This information can come from data sources 130 such as clinical notes, lab test results, information reported by the patient, medical images, clinical trial publications, etc. The generated sequences are then hashed by the corresponding data source-specific hash functions. Longitudinal sequences can be generated from any information collected at two or more intervals (e.g., at yearly physical examinations, continuously by a wearable fitness tracking device, from irregular patient check-ins, etc.). Examples of longitudinal sequences are discussed in greater detail below.

The training module 110 then uses data source-specific hash functions to generate hash codes for each of the extracted features. These hash functions can be represented by equation 1:

$$\mathcal{H}_f^n : f^n \to C_{\mathcal{H}}^n (f^n) \tag{1}$$

where H is a data source-specific hash function that produces hash codes (C) for a feature set (f) from a data source, and where n indicates the number of the data source 130 (e.g., n=1, 2, 3, etc.). Continuing the example above in which the data sources 130 include an MRI scan database (n=1) and a CT scan database (n=2), the training module 110 can use a first data source-specific hash function ($H^1$) on the MRI scan features ($f^1$), and a second data source-specific hash function ($H^2$) on the CT scan features ($f^2$). The training module 110 uses the data source-specific hash functions to generate groups of hash codes ($C^1$ and $C^2$, respectively) for each data source.

The hash codes from the different data sources 130 can be aggregated. For example, the hash codes can be aggregated by taking the union of $$C_{h_{f_1}^1}(f^1), \ldots, C_{h_{f_n}^n}(f^n)$$

for underlying data sources 130 (X). The training module 110 can use at least one superclass hash function (Hx) to hash the aggregated hash codes. This hash function can be represented by equation 2:

$$\mathcal{H}_X : \underbrace{\bigcup f^n}_{X_N} \rightarrow \underbrace{\bigcup \left\{ C_{h_{f_1}^1}(f^1), \ldots, C_{h_{f_n}^n}(f^n) \right\}}_{C_{\mathcal{H}_X}(X_N)} \quad (2)$$

where N represents a number of levels. For example, N=1 when each of the aggregated hash codes has been generated by a data source-specific hash function (equation 1). Continuing the example above, the hash codes of the MRI and CT scan databases ($X_1$) can be hashed by a first superclass hash function. A second superclass hash function can be used to hash aggregated hash codes from a second group of data sources 130 ($X_2$). The hash codes generated by the first and second superclass hash functions can then be aggregated, and hashed by a higher level superclass hash function (N=3).

The training module 110 can therefore use superclass hash functions to obtain training data from a large number of sources 130 without storing the training data in a centralized location. Information from the data sources 130 is extracted, and features of each data point (e.g., features in original space, feature space, latent space, etc.) are hashed by data source-specific hash functions. The resulting hash codes are hashed by a superclass hash function. Additional superclass hash functions can be used on hash codes generated by lower level superclass hash functions. This allows features to be encoded at multiple levels. The training module 110 can maintain the position of each hash code with respect to n (equation 1). For example, the first four bits of each hash code can be allocated to the first source (n=1) in the first level (N=1). In some embodiments, the training module 110 generates vectors of the hash codes, and uses these vectors as training data.

The superclass hash functions can be defined for hash codes aggregated from data sources 130 according to preset and/or user-selected categories. For example, there can be at least one superclass hash function for a group of medical imaging data sources. The data sources 130 can include at least one type of medical image from at least one database or institution. For example, a group of fifteen data sources 130 can include X-ray image, MRI scan, and CT scan databases from five different healthcare providers. Various superclass hash functions can be used on hash codes from these data sources 130. For example, a superclass hash function can be generated for the five X-ray image data sources 130, each having hash codes hashed by a different data source-specific hash function. Similarly, superclass hash functions can be generated for the five MRI scan databases and the five CT scan databases. At least one higher level superclass hash function can be generated as well. For example, there can be a superclass hash function for the medical imaging category. This superclass hash function can be used on aggregated hash codes generated by the three lower level superclass hash functions.

However, any categories can be defined for grouping data sources 130. For example, the medical imaging data sources 130 can be categorized by type of information. That is, there can be a superclass hash function for spinal medical images that include both X-ray images and CT scans from multiple data sources 130. In some embodiments, there can be a lower level superclass hash function for the spinal X-rays and a lower level superclass hash function for the CT scans. In other embodiments, the hash codes representing spinal features generated by data source-specific hash functions for both the X-ray image and CT scan databases can be hashed by a single superclass hash function for the category spinal imaging. Additionally, there can be a higher level superclass hash function for medical imaging that includes the spinal imaging hash codes and hash codes generated by superclass hash functions for other types of information, such as breast cancer screening images from MRI scans, CT scans, and mammograms.

If new features are provided by a data source, the new features can be hashed by the corresponding data source-specific hash function, and the resulting hash codes can be hashed by any associated superclass hash functions. If new data sources 130 are added, the training module can hash features from the new data sources 130 with a new data source-specific hash function. Hash codes generated by one or more new data source-specific hash functions can be hashed by a new or existing superclass hash function. In some embodiments, a new data source 130 can be added by aggregating hash codes from its associated data source-specific hash function with hash codes generated by a higher level superclass hash function. Additionally, new groups of data sources 130 can be defined in some embodiments, and a new superclass hash function can be used on hash codes generated by the new data source-specific hash functions.

The retrieval module 115 includes machine learning models trained on the training data (e.g., hash codes) generated by the training module 110 at each level. This can be carried out in a variety of ways. In some embodiments, vectors are generated for sets of hash codes, such as those generated by equation 2. The length of each vector can be equal to the number of data sources 130 (X). When a vector is generated, it is labeled and used as training data for the retrieval module 115. Additional vectors can be generated for hash codes generated by superclass hash functions. Examples of techniques that can be used to train the machine learning model can include any appropriate supervised or unsupervised learning techniques, such as random forest, convolutional neural networks, locality-sensitive hashing (LSH), kernelized LSH, spectral hashing, anchor graph hashing, etc.

The retrieval module 115 determines the similarity between new data and the training data from the data sources 130. This is discussed in greater detail with respect to FIG. 2. The new data can be case data 140 entered by a medical professional through the user interface 125. For example, a doctor may want to plan a treatment for a patient with scoliosis. The doctor can enter case data 140 for the patient such as medical images (e.g., spinal CT and/or MRI scans, spinal X-ray images, etc.). Other case data 140 can be entered as well, such as patient background (e.g., age, sex, other known health conditions, prescriptions, treatment history, family medical history, etc.) and/or wellness information (e.g., blood pressure, body mass index, lab test results, etc.).

The plan generator 120 extracts features from the case data 140. These can include features such as those extracted from the training data. In some embodiments, the features are directly input via the user interface 125. However, features can also be extracted from a patient's medical records if the plan generator 120 is authorized to access the records. In some embodiments, the plan generator 120 generates at least one longitudinal sequence from the case data 140.

For example, the patient with scoliosis may have regular CT scans. The case data 140 can include information from these CT scans, such as image features and/or data such as degrees of spinal curvature (e.g., Cobb angle). Using this information, the plan generator 120 can generate a longitudinal sequence representing rates of change in curvature over time. For example, the patient may be 32-year-old male diagnosed with scoliosis in early adolescence. Since that time, the patient may have had yearly CT scans showing a gradual and steady increase in Cobb angle until early adulthood, followed by a greater rate of change for several years. However, the most recent CT scans may show that there has been no change in the past three years. The plan generator 120 can extract features from the case data 140 that include measures of these changes, as well as background information (e.g., age, sex, other medical conditions, family history of scoliosis, etc.) and wellness information collected at the time of each CT scan (e.g., height, weight, blood pressure, reported symptoms such as back pain or shortness of breath, etc.). The plan generator 120 can measure longitudinal features based on changes in the wellness information over time as well.

The retrieval module 115 hashes features extracted by the plan generator 120 using at least one hash function from the training module 110. Similarities between features or combinations of features can be determined at any of the training data levels by generating query hash codes with the corresponding superclass hash functions or data source-specific hash functions. Training data hash codes ($C_i$, where i represents the level) can be compared to hash codes generated for the case data 140 query ($C_{qi}$) using any appropriate similarity determining techniques. For example, the retrieval module 115 may locate similar patients using a superclass hash function (e.g., a patient-level hash function) to hash patient features from the case data 140. The Hamming distance between each hash code in training data generated by the patient-level superclass hash function and a query hash code ($C_{pi} \oplus C_{qi}$) can be calculated. In some embodiments, when more than one data source 130 is queried, the most similar training data hash codes can be found by minimizing the root square error between generated hash codes at each level.

Returning to the example above, a superclass hash function can be used to find cases above a similarity threshold to that of the 32-year-old male with scoliosis (e.g., based on a patient background information level, men with scoliosis who are 32±5 years). The similarities can be calculated at additional levels. For example, medical imaging features from the case data 140 can be hashed with at least one superclass hash function for medical images to determine similarities between features such as current angles of curvature, as well as longitudinal features such as rates of change in curvature over time. Additional examples of features that can be compared are discussed in greater detail above.

When at least one patient with similarities above a threshold similarity is located, the plan generator 120 can identify treatment options and calculate outcome probabilities for these treatments. The plan generator 120 can also calculate probabilities to aid in diagnosis and/or evaluation of a health condition. In the above example, there can be a group of twenty patients similar to the patient associated with the case data 140. If ten of these patients were treated with surgery to reduce spinal curvature, the outcomes of these surgeries can be compared. For example, if seven of the patients had future CT scans showing that the reduced curvature was maintained, and three had future CT scans showing increased spinal curvature, the probability of surgery being a successful option may be 70%. Further, if the training data indicated that 19 of the similar patients had been experiencing back pain for a given amount of time, and that 8 of the 10 patients who had surgery reported pain reduction while the remaining 12 patients reported either an increase or no change in back pain, the plan generator 120 may determine that surgery has an even greater probability of success.

The plan generator 120 generates and delivers a report via the user interface 125. The report can indicate a variety of information, including treatment options and probabilities of success. Additional details can be provided as well. For example, the report can indicate the sample size (e.g., 20 patients), the similarity values (e.g., based on Hamming distances), the types of data considered (e.g., CT scans, age, sex, longitudinal features such as curvature and symptom development), indicators of success (e.g., reduced pain and maintenance of curve reduction), etc. This can allow the medical professional and patient to make informed decisions regarding which treatment options to follow.

Figure 2:
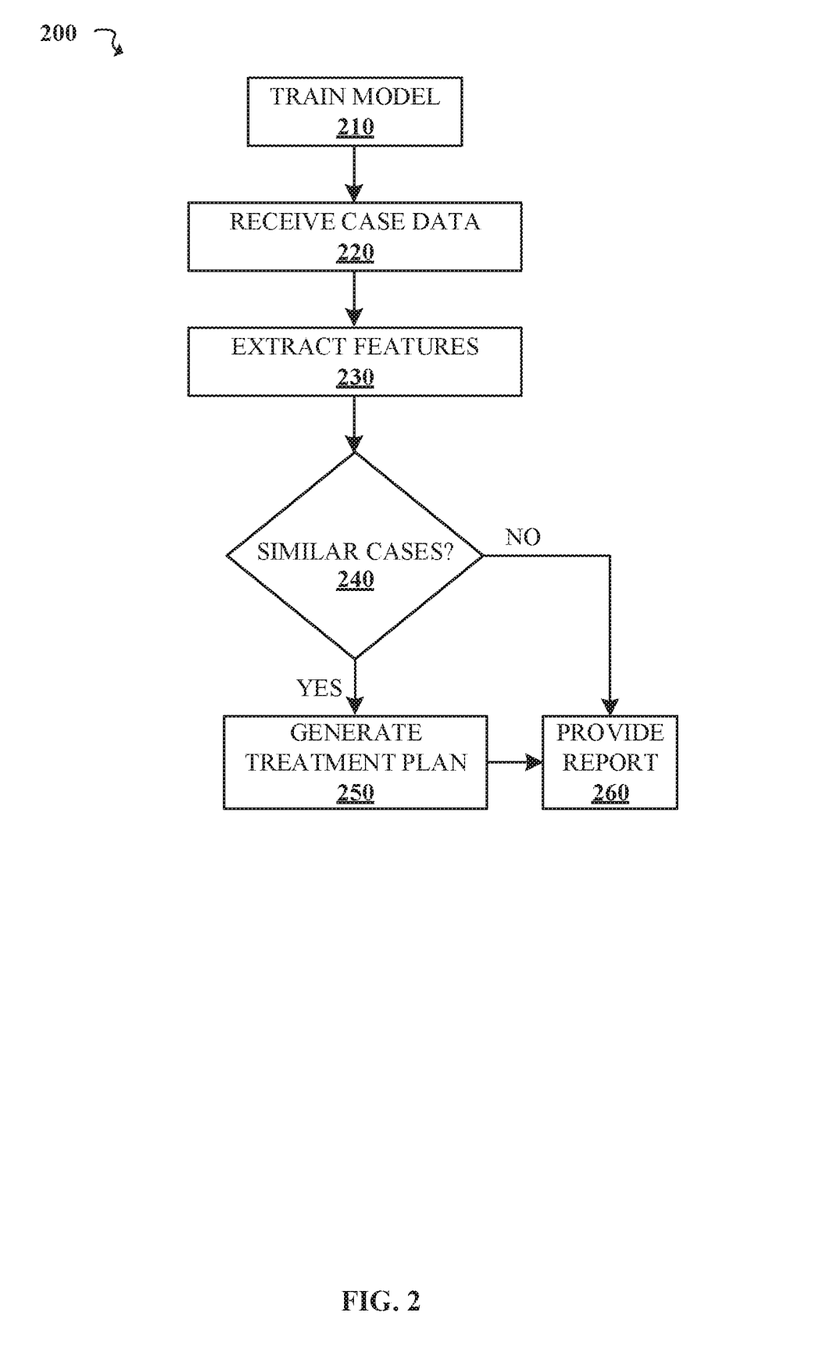
FIG. 2 is a flow diagram illustrating a process of generating a treatment plan, according to some embodiments of the present disclosure.

FIG. 2 is a flow diagram illustrating a process 200 of generating a treatment plan, according to some embodiments of the present disclosure. To illustrate process 200, but not to limit embodiments, FIG. 2 is described within the context of the treatment planning environment 100 of FIG. 1. Where elements referred to in FIG. 2 are identical to elements shown in FIG. 1, the same reference numbers are used in both Figures.

A machine learning model is trained. This is illustrated at operation 210. Training data for the model is generated by the training module 110. The training module extracts features from data sources 130, and hashes these features using data source-specific hash functions (equation 1). In some embodiments, the features include longitudinal sequences calculated from series of data collected for one patient over a period of time. Superclass hash functions (equation 2) can be generated for various categories (e.g., wellness information, patient background information, medical images, etc.), and used to hash the hash codes generated by the data source-specific hash functions. Examples of extracted features and superclass hash function categories are discussed in greater detail with respect to FIG. 1.

Additional superclass hash functions can be used on hash codes generated by lower level superclass hash functions. In some embodiments, the hash codes are used as training data. In other embodiments, the training data includes vectors generated from sets of the hash codes. Examples of techniques that can be used to train the machine learning model can include any appropriate supervised or unsupervised learning techniques, such as random forest, convolutional neural networks, locality-sensitive hashing (LSH), kernelized LSH, spectral hashing, anchor graph hashing, etc.

Case data 140 for a patient is entered. This is illustrated at operation 220. The case data 140 includes information specific to a patient for whom a treatment is being planned, and can be entered by a user (e.g., a qualified medical professional) and/or automatically extracted from a patient's medical records by the plan generator 120, if given access to these records. Examples of case data 140 can include X-ray and/or other medical images, prescription records, electrocardiogram (EKG) results, lab test results, data from physical examinations (e.g., height, weight, body mass index, visual acuity, etc.), clinical notes, and any other relevant data. (e.g., known allergies, family medical history, measures of diet, exercise, and sleep, etc.). The data can be collected by at least one medical professional. In some embodiments, case data 140 can also be self-reported and/or based on fitness data from mobile devices (e.g., wearable devices or smartphones) with fitness tracking features (e.g., motion sensors, heart rate monitors, speedometers, etc.).

The plan generator 120 extracts features from the case data 140. This is illustrated at operation 230. These features can include features from images, text, information such as the date and time of data collection, the type/model of instrument and data collection settings (e.g., X-ray frequency, instrument manufacturer, etc.), numerical values, etc. In some embodiments, the user indicates which features to extract. For example, the user can enter data (e.g., numerical values and/or text) into designated fields in the user interface 125 (e.g., fields for entering information such as patient name, age, lab test results, etc.). There can also be a field for uploading text and/or image files (e.g., clinical notes, medical images, etc.).

In some embodiments, the user can click on or otherwise highlight a region of interest in a medical image. Features of this image can then be extracted by the plan generator 120. In other embodiments, regions of interest can be automatically identified by the plan generator 120 based on recognition of image features (e.g., characteristics of legions, anatomical features, etc.). Similarly, features can be automatically extracted from text based on techniques such as keyword recognition, natural language processing, etc. For example, the case data 140 can include at least one MRI intended to assess and characterize breast abnormalities. The plan generator 120 can extract image features from region(s) of interest that may include abnormalities (e.g., lesions). The image features can include volumetric data, morphological features, boundaries of an abnormality, etc. Additionally, when the case data 140 includes a series of MRIs showing the region of interest, longitudinal sequences can be generated for changes in the image features.

It is then determined whether there are cases with features similar to that of the case data 140. This is illustrated at operation 240. To identify patients such as these, the retrieval module 115 can compare hashed features of the case data 140 with hashed features from the data sources 130. The comparisons are made by determining similarities between hash codes at various levels. To search a level, the retrieval module 115 generates a query hash code by hashing a feature from the case data 140 with a superclass hash function corresponding to the level. This can be carried out for multiple features, and at multiple levels. Query hash codes can also be generated for data source-specific hash functions. The query hash codes can optionally be added to the training data (operation 210).

Hash codes from the training data with similarity values above threshold similarities to the query hash codes can be selected in some embodiments. In other embodiments, a given number of hash codes from the training data having the closest similarities to the query hash codes can be selected. The case matching specificity can be increased by evaluating features at multiple levels. For example, if patients with similar background information do not also have similar features at another level (e.g., medical imaging), these patients' cases may be removed from the group of similar cases. The different levels can optionally have different similarity thresholds. In some embodiments, similar features must be found at specific levels (e.g., patient background information, wellness data, and at least one type of medical imaging data), although there can also be a minimum number of similarity features and/or a minimum number of levels required to be selected as a similar case.

If similar cases have been identified, a treatment plan can be generated. This is illustrated at operation 250. The probabilities can be determined by evaluating the known outcomes of treatments, the progression of symptoms (e.g., based on longitudinal sequence features), and other results from the similar cases. Returning to the above example involving breast abnormality MRIs, features such as volumetric data, morphological features, boundaries of an abnormality, and longitudinal sequence(s) from similar cases with known outcomes can be evaluated. The plan generator 120 then generates the treatment plan based on these predicted outcomes. The treatment plan can also provide information for diagnosis and/or prognosis of a health condition. These can also be based on comparison with known outcomes of similar cases.

If no similar cases are identified at operation 240, or if a treatment plan has been generated at operation 250, a report can be provided to the user. This is illustrated at step 260. If no similar cases were found, the report can indicate this. The report can also suggest information that may be added to or removed from the case data 140, thereby returning the user to operation 220. When a treatment plan has been generated, the report can illustrate the plan by providing a variety of information, such as outcome probabilities, search and/or evaluation parameters, sample size, etc. Examples of this information are discussed in greater detail with respect to FIG. 1. The user can optionally return to operation 220 after viewing the report, and make changes to the case data 140 (e.g., if new data is received or if the user wishes to view another plan based on alternative information). The report can optionally provide fields for entering different case data 140 or adjusting the search and/or evaluation parameters. In some embodiments, process 200 can end after the report has been generated.

Figure 3:
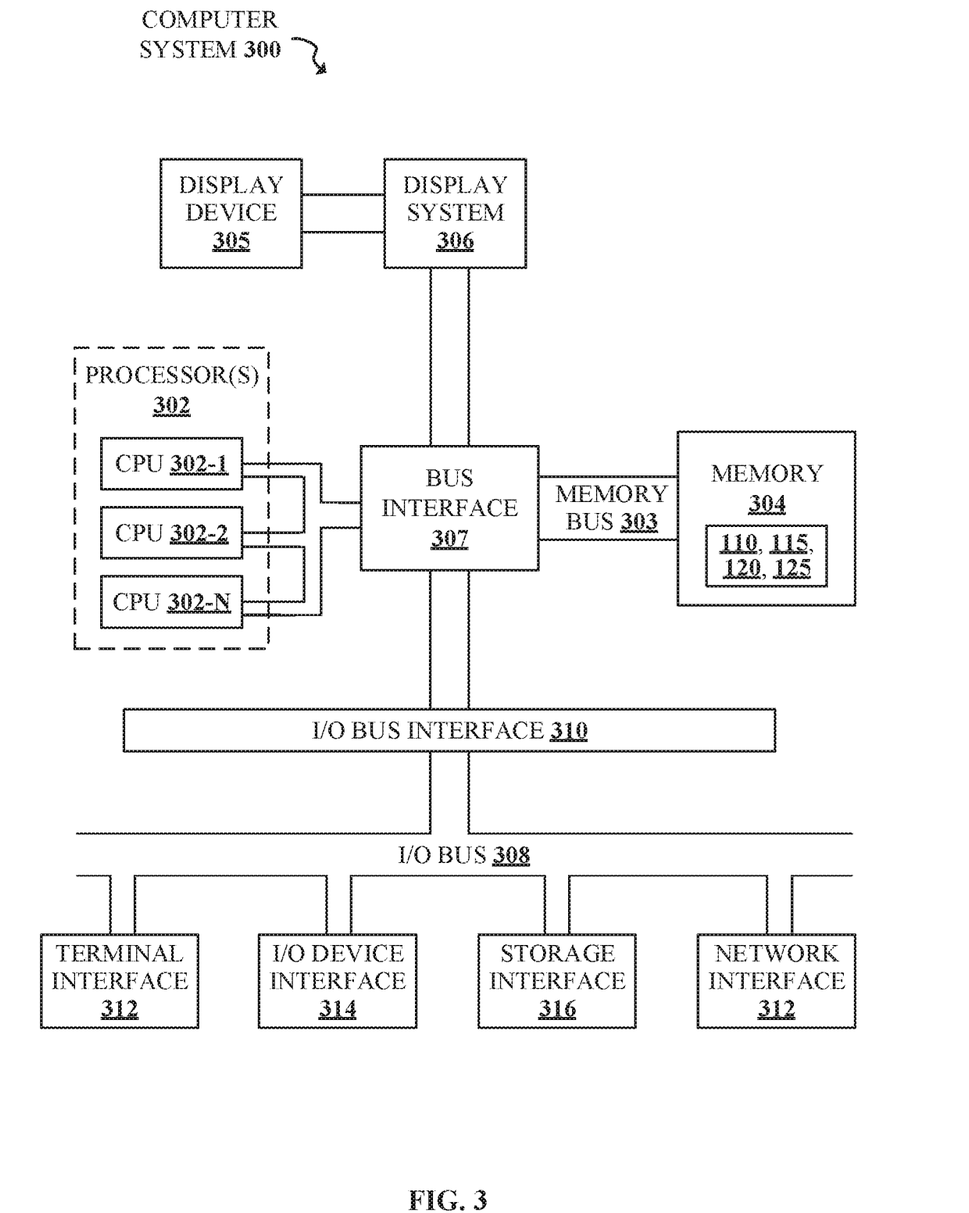
FIG. 3 is a block diagram illustrating a computer system, according to some embodiments of the present disclosure.

FIG. 3 is a block diagram illustrating an exemplary computer system 300 that can be used in implementing one or more of the methods, tools, components, and any related functions described herein (e.g., using one or more processor circuits or computer processors of the computer). In some embodiments, the major components of the computer system 300 comprise one or more processors 302, a memory subsystem 304, a terminal interface 312, a storage interface 316, an input/output device interface 314, and a network interface 318, all of which can be communicatively coupled, directly or indirectly, for inter-component communication via a memory bus 303, an input/output bus 308, bus interface unit 307, and an input/output bus interface unit 310.

The computer system 300 contains one or more general-purpose programmable central processing units (CPUs) 302-1, 302-2, and 302-N, herein collectively referred to as the CPU 302. In some embodiments, the computer system 300 contains multiple processors typical of a relatively large system; however, in other embodiments the computer system 300 can alternatively be a single CPU system. Each CPU 302 may execute instructions stored in the memory subsystem 304 and can include one or more levels of on-board cache.

The memory 304 can include a random-access semiconductor memory, storage device, or storage medium (either volatile or non-volatile) for storing or encoding data and programs. In some embodiments, the memory 304 represents the entire virtual memory of the computer system 300, and may also include the virtual memory of other computer systems coupled to the computer system 300 or connected via a network. The memory 304 is conceptually a single monolithic entity, but in other embodiments the memory 304 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory can be further distributed and associated with different CPUs or sets of CPUs, as is known in any of various so-called non-uniform memory access (NUMA) computer architectures.

These components are illustrated as being included within the memory 304 in the computer system 300. However, in other embodiments, some or all of these components may be on different computer systems and may be accessed remotely, e.g., via a network. The computer system 300 may use virtual addressing mechanisms that allow the programs of the computer system 300 to behave as if they only have access to a large, single storage entity instead of access to multiple, smaller storage entities. Thus, though the training module 110, retrieval module 115, plan generator 120, and user interface 125 (FIG. 1) are illustrated as being included within the memory 304, components of the memory 304 are not necessarily all completely contained in the same storage device at the same time. Further, although these components are illustrated as being separate entities, in other embodiments some of these components, portions of some of these components, or all of these components may be packaged together.

In an embodiment, the training module 110, retrieval module 115, plan generator 120, and user interface 125 include instructions that execute on the processor 302 or instructions that are interpreted by instructions that execute on the processor 302 to carry out the functions as further described in this disclosure. In another embodiment, the training module 110, retrieval module 115, plan generator 120, and user interface 125 are implemented in hardware via semiconductor devices, chips, logical gates, circuits, circuit cards, and/or other physical hardware devices in lieu of, or in addition to, a processor-based system. In another embodiment, the training module 110, retrieval module 115, plan generator 120, and user interface 125 include data in addition to instructions.

Although the memory bus 303 is shown in FIG. 3 as a single bus structure providing a direct communication path among the CPUs 302, the memory subsystem 304, the display system 306, the bus interface 307, and the input/output bus interface 310, the memory bus 303 can, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the input/output bus interface 310 and the input/output bus 308 are shown as single respective units, the computer system 300 may, in some embodiments, contain multiple input/output bus interface units 310, multiple input/output buses 308, or both. Further, while multiple input/output interface units are shown, which separate the input/output bus 308 from various communications paths running to the various input/output devices, in other embodiments some or all of the input/output devices may be connected directly to one or more system input/output buses.

The computer system 300 may include a bus interface unit 307 to handle communications among the processor 302, the memory 304, a display system 306, and the input/output bus interface unit 310. The input/output bus interface unit 310 may be coupled with the input/output bus 308 for transferring data to and from the various input/output units. The input/output bus interface unit 310 communicates with multiple input/output interface units 312, 314, 316, and 318, which are also known as input/output processors (IOPs) or input/output adapters (IOAs), through the input/output bus 308. The display system 306 may include a display controller. The display controller may provide visual, audio, or both types of data to a display device 305. The display system 306 may be coupled with a display device 305, such as a standalone display screen, computer monitor, television, or a tablet or handheld device display. In alternate embodiments, one or more of the functions provided by the display system 306 may be on board a processor 302 integrated circuit. In addition, one or more of the functions provided by the bus interface unit 307 may be on board a processor 302 integrated circuit.

In some embodiments, the computer system 300 is a multi-user mainframe computer system, a single-user system, or a server computer or similar device that has little or no direct user interface, but receives requests from other computer systems (clients). Further, in some embodiments, the computer system 300 is implemented as a desktop computer, portable computer, laptop or notebook computer, tablet computer, pocket computer, telephone, smart phone, network switches or routers, or any other appropriate type of electronic device.

It is noted that FIG. 3 is intended to depict the representative major components of an exemplary computer system 300. In some embodiments, however, individual components may have greater or lesser complexity than as represented in FIG. 3, Components other than or in addition to those shown in FIG. 3 may be present, and the number, type, and configuration of such components may vary.

In some embodiments, the data storage and retrieval processes described herein could be implemented in a cloud computing environment, which is described below with respect to FIGS. 4 and 5. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring humale interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
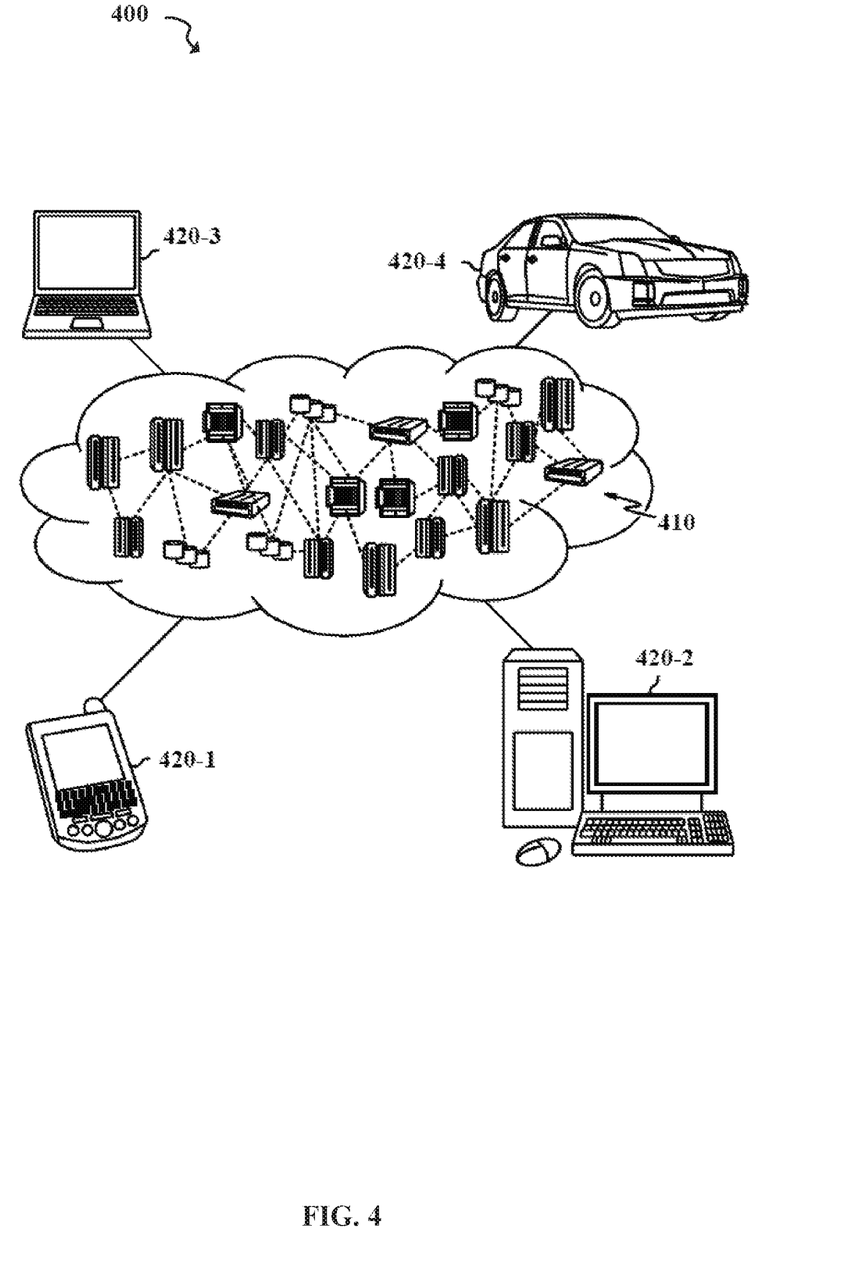
FIG. 4 is a block diagram illustrating a cloud computing environment, according to some embodiments of the present disclosure.

FIG. 4 is a block diagram illustrating a cloud computing environment 400, according to some embodiments of the present disclosure. As shown, cloud computing environment 400 includes one or more cloud computing nodes 410 with which local computing devices used by cloud consumers, such as, for example, personal digital assistant (PDA) or cellular telephone 420-1, desktop computer 420-2, laptop computer 420-3, and/or automobile computer system 420-4 may communicate. Nodes 410 may communicate with one another. They may be grouped (not shown) physically or virtually, in one or more networks, such as Private, Community, Public, or Hybrid clouds as described hereinabove, or a combination thereof. This allows cloud computing environment 400 to offer infrastructure, platforms and/or software as services for which a cloud consumer does not need to maintain resources on a local computing device. It is understood that the types of computing devices 420-1-420-4 shown in FIG. 4 are intended to be illustrative only and that computing nodes 410 and cloud computing environment 400 can communicate with any type of computerized device over any type of network and/or network addressable connection (e.g., using a web browser).

Figure 5:
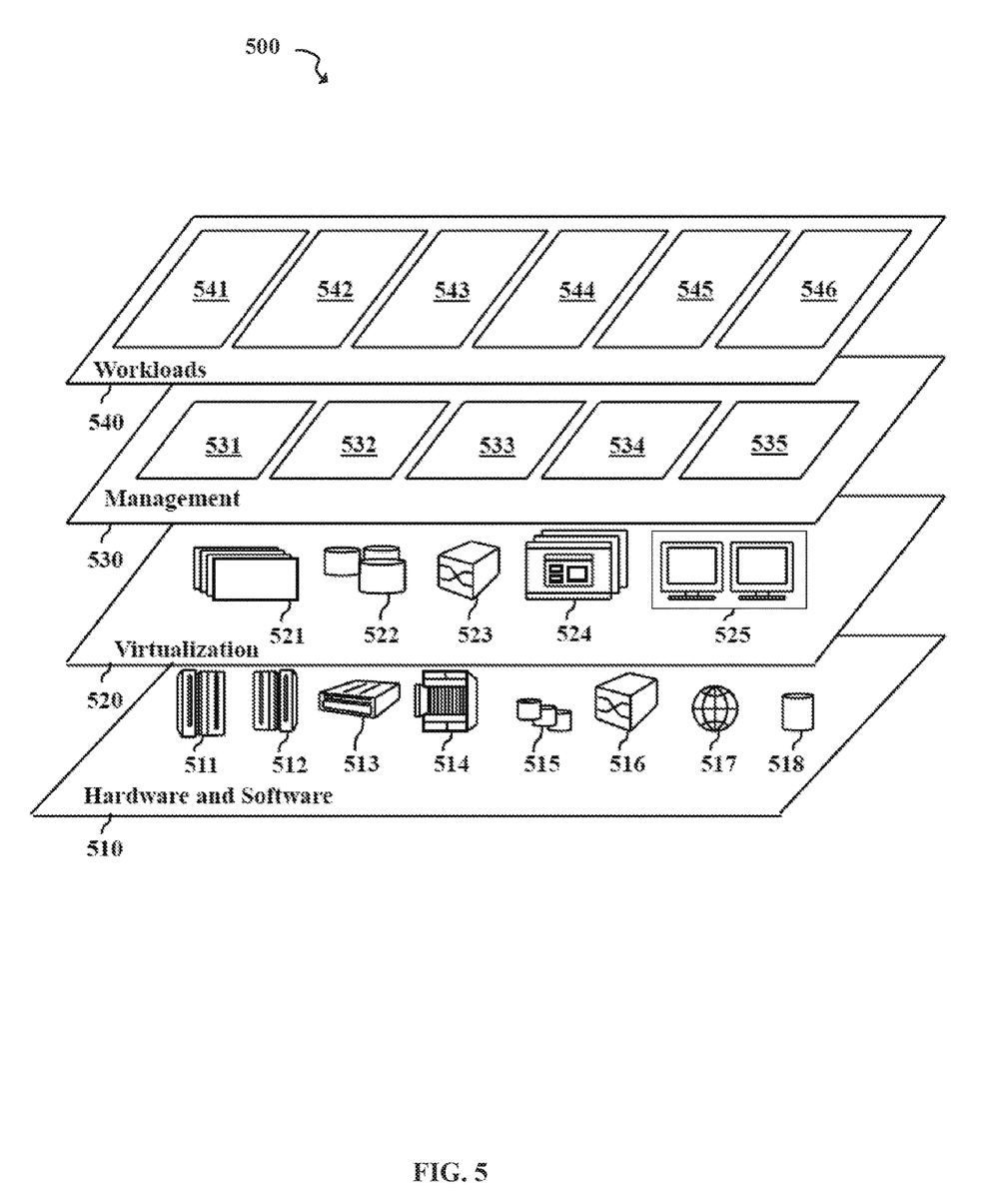
FIG. 5 is a block diagram illustrating a set of functional abstraction model layers provided by the cloud computing environment, according to some embodiments of the present disclosure.

FIG. 5 is a block diagram illustrating a set of functional abstraction model layers 500 provided by the cloud computing environment 400, according to some embodiments of the present disclosure. It should be understood in advance that the components, layers, and functions shown in FIG. 5 are intended to be illustrative only and embodiments of the invention are not limited thereto. As depicted, the following layers and corresponding functions are provided:

Hardware and software layer 510 includes hardware and software components. Examples of hardware components include: mainframes 511; RISC (Reduced Instruction Set Computer) architecture-based servers 512; servers 513; blade servers 514; storage devices 515; and networks and networking components 516. In some embodiments, software components include network application server software 517 and database software 518.

Virtualization layer 520 provides an abstraction layer from which the following examples of virtual entities may be provided: virtual servers 521; virtual storage 522; virtual networks 523, including virtual private networks; virtual applications and operating systems 524; and virtual clients 525.

In one example, management layer 530 provides the functions described below. Resource provisioning 531 provides dynamic procurement of computing resources and other resources that are utilized to perform tasks within the cloud computing environment. Metering and Pricing 532 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 533 provides access to the cloud computing environment for consumers and system administrators. Service level management 534 provides cloud computing resource allocation and management such that required service levels are met. Service Level Agreement (SLA) planning and fulfillment 535 provide pre-arrangement for, and procurement of, cloud computing resources for which a future requirement is anticipated in accordance with an SLA.

Workloads layer 540 provides examples of functionality for which the cloud computing environment can be utilized. Examples of workloads and functions that can be provided from this layer include: mapping and navigation 541; software development and lifecycle management 542; virtual classroom education delivery 543; data analytics processing 544; transaction processing 545; and generating treatment plans based on multimodal training data 546.

The present disclosure may be a system, a method, and/or a computer program product. The computer program product may include a computer readable storage medium (or media) having computer readable program instructions thereon for causing a processor to carry out aspects of the present disclosure.

The computer readable storage medium is a tangible device that can retain and store instructions for use by an instruction execution device. Examples of computer readable storage media can include an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a component, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the present disclosure.

What is claimed is:

1. A system, comprising:
    at least one processing component;
    at least one memory component;
    a training module configured to:
        generate data source specific hash codes by hashing features from two or more data sources with data source-specific hash functions, wherein there is a different data source-specific hash function for different ones of the two or more data sources; and
        generate superclass hash codes by hashing the generated data source-specific hash codes with at least one superclass hash function;
    a retrieval module configured to:
        extract features from case data; and
        locate features from at least one of the two or more data sources that are similar to the extracted features based on a query hash code generated by executing at least one hash function on the extracted features from the case data, and a comparison of the query hash code with one or more of the at least one superclass hash function or the data source-specific hash codes; and
    a plan generator configured to:
        calculate outcome probabilities for the case data based on known outcomes associated with the located features.

2. The system of claim 1, wherein the features from the two or more data sources include at least one longitudinal sequence.

3. The system of claim 1, wherein the extracted features include at least one longitudinal sequence, and wherein the at least one longitudinal sequence is based on a series of medical images.

4. The system of claim 1, wherein the training module is further configured to generate a machine learning model trained on the superclass hash codes.

5. The system of claim 1, wherein the retrieval module is further configured to generate the query hash code by hashing a feature from the extracted features with the at least one superclass hash function.

6. The system of claim 1, wherein the training module is further configured to generate higher level superclass hash codes by hashing a group of the superclass hash codes with at least one higher level superclass hash function.

7. The system of claim 6, wherein the training module is further configured to generate a machine learning model trained on the at least one higher level superclass hash codes.

8. The system of claim 6, wherein the retrieval module is further configured to generate the query hash code by hashing a feature from the extracted features with the at least one higher level superclass hash function.

9. A method of treatment planning, comprising:
    generating data source specific hash codes by hashing features from two or more data sources with data source-specific hash functions, wherein there is a different data source-specific hash function for different ones of the two or more data sources;
    generating hash codes by hashing the generated data source-specific hash codes with at least one superclass hash function;
    extracting features from case data;
    locating features from at least one of the two or more data sources that are similar to the extracted features based on a query hash code generated by executing at least one hash function on the extracted features from the case data, and a comparison of the query hash code with one or more of the at least one superclass hash function or the data source-specific hash codes; and
    calculating outcome probabilities for the case data based on known outcomes associated with the located features.

10. The method of claim 9, wherein the features from the two or more data sources include at least one longitudinal sequence.

11. The method of claim 9, wherein the extracted features include at least one longitudinal sequence, and wherein the at least one longitudinal sequence is based on a series of medical images.

12. The method of claim 9, further comprising generating a machine learning model trained on the superclass hash codes.

13. The method of claim 9, further comprising generating the query hash code by hashing a feature from the extracted features with the at least one superclass hash function.

14. The method of claim 9, further comprising generating higher level superclass hash codes by hashing a group of the superclass hash codes with at least one higher level superclass hash function.

15. The method of claim 14, further comprising generating the query hash code by hashing a feature from the extracted features with the at least one higher level superclass hash function.

16. The method of claim 9, wherein the superclass hash codes are generated at least by aggregating the data source-specific hash codes by taking a union of the data source-specific hash codes and executing the at least one superclass hash function on the union of the data source-specific hash codes.

17. The method of claim 9, wherein the at least one superclass hash function comprises a plurality of different superclass hash functions, and wherein each different superclass hash function is associated with a different category of data sources.

18. The method of claim 17, wherein the different categories of data sources comprise different types of medical imaging modalities such that there is a different superclass hash function for each of the different types of medical imaging modalities.

19. A computer program product for treatment planning, the computer program product comprising a computer readable storage medium having program instructions embodied therewith, the program instructions executable by a processor to cause a device to perform a method, the method comprising:
    generating data source specific hash codes by hashing features from two or more data sources with data source-specific hash functions, wherein there is a different data source-specific hash function for different ones of the two or more data sources;

generating hash codes by hashing the generated data source-specific hash codes with at least one superclass hash function;

extracting features from case data;

locating features from at least one of the two or more data sources that are similar to the extracted features based on a query hash code generated by executing at least one hash function on the extracted features from the case data, and a comparison of the query hash code with one or more of the at least one superclass hash function or the data source-specific hash codes; and calculating outcome probabilities for the case data based on known outcomes associated with the located features.

20. The computer program product of claim 19, further comprising generating higher level superclass hash codes by hashing a group of the superclass hash codes with at least one higher level superclass hash function.

\* \* \* \* \*